United States Patent [19]

Hardy et al.

[11] 3,965,907

[45] June 29, 1976

[54] SURGICAL SPONGE

[75] Inventors: David R. Hardy; Richard C. Weatherford, both of Augusta, Ga.

[73] Assignee: The Kendall Company, Boston, Mass.

[22] Filed: Jan. 8, 1975

[21] Appl. No.: 539,358

[52] U.S. Cl. ............................ 128/296; 128/269; 128/290 W
[51] Int. Cl.² .................. A61M 35/00; A61F 13/00
[58] Field of Search ............... 128/269, 268, 290 W, 128/296; 401/132

[56] References Cited
UNITED STATES PATENTS

| | | | |
|---|---|---|---|
| 2,294,186 | 8/1942 | Kirschbaum | 128/269 |
| 2,972,350 | 2/1961 | Deker | 128/296 |
| 3,464,415 | 9/1969 | Brownlee | 128/296 |
| 3,495,917 | 2/1970 | Truhan | 401/132 |
| 3,756,241 | 9/1973 | Patience | 128/296 |
| 3,837,950 | 9/1974 | Reimels | 156/73 |

Primary Examiner—Aldrich F. Medbery
Attorney, Agent, or Firm—Powell L. Sprunger

[57] ABSTRACT

A surgical sponge comprising, an absorbent fabric, and an X-ray detectable element integrally bonded to fibers in the fabric. The element has a distinctive configuration to provide a recognizable pattern on an X-ray photograph.

14 Claims, 14 Drawing Figures

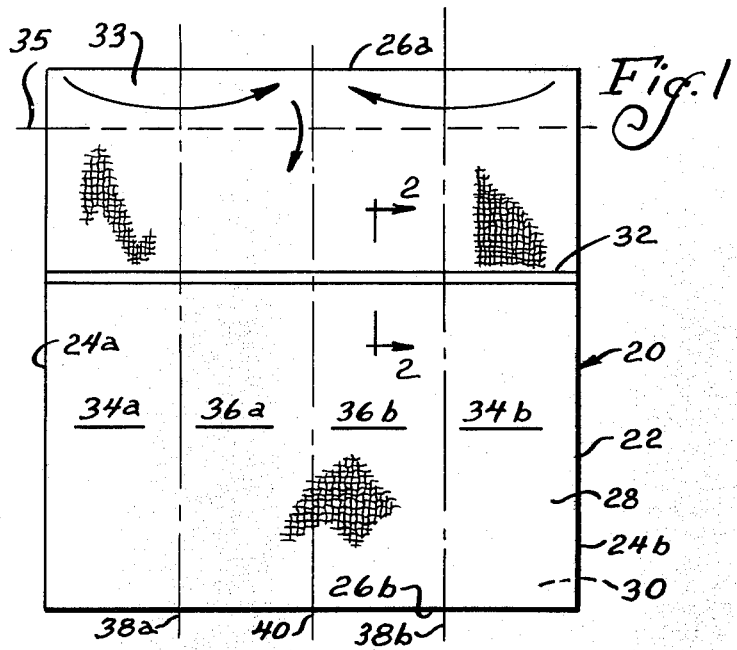
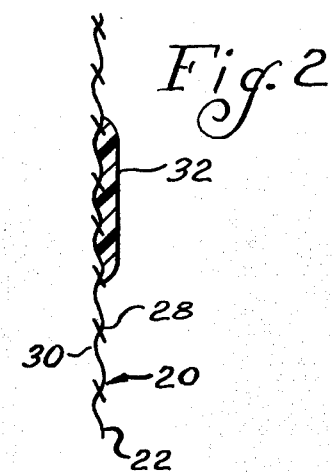
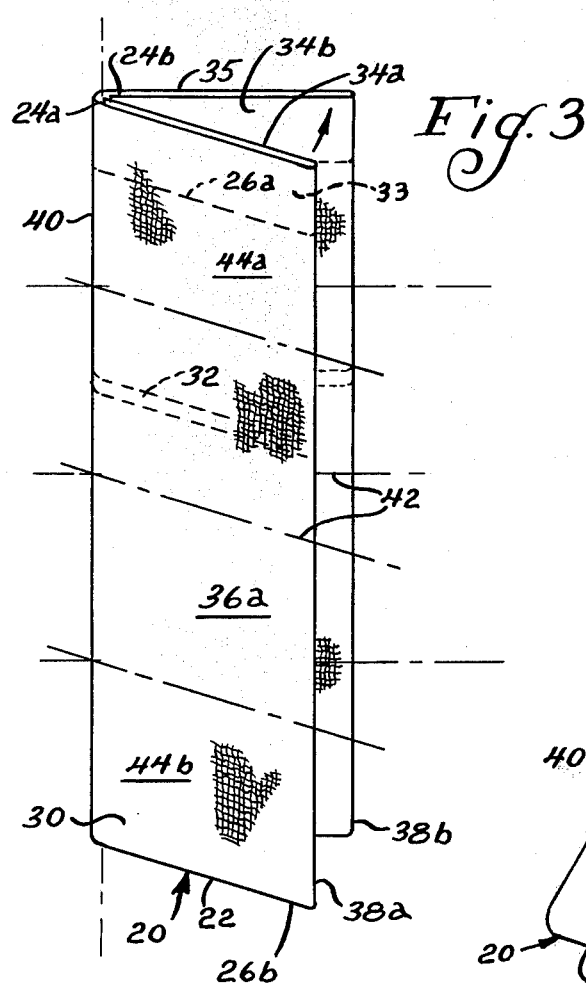
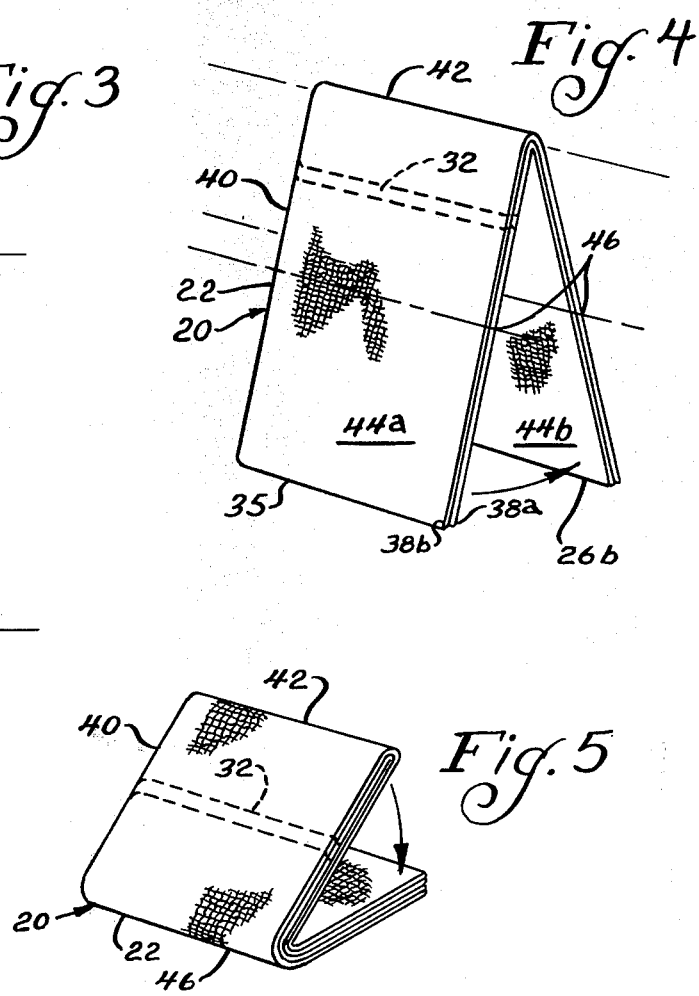
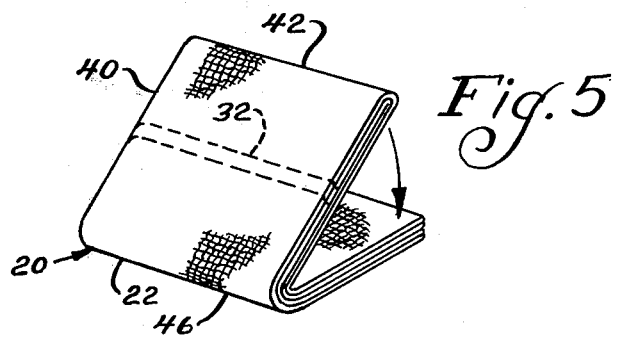

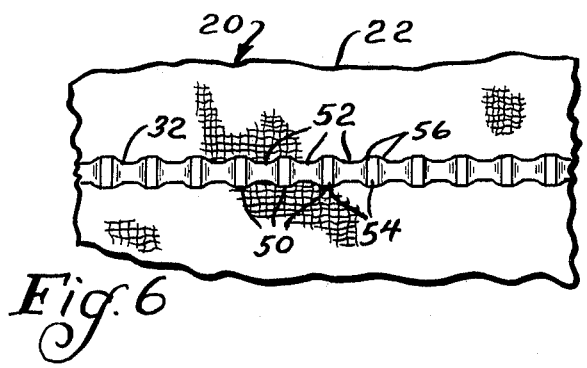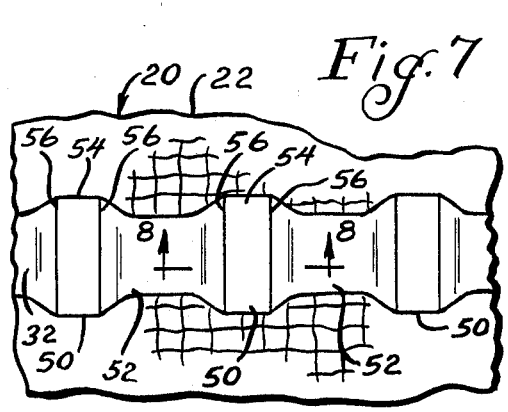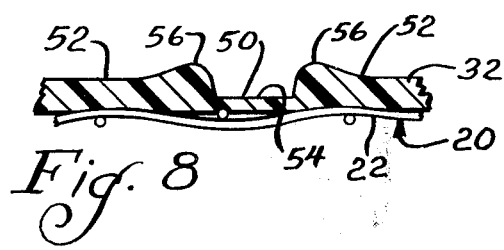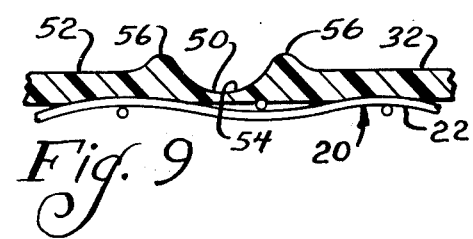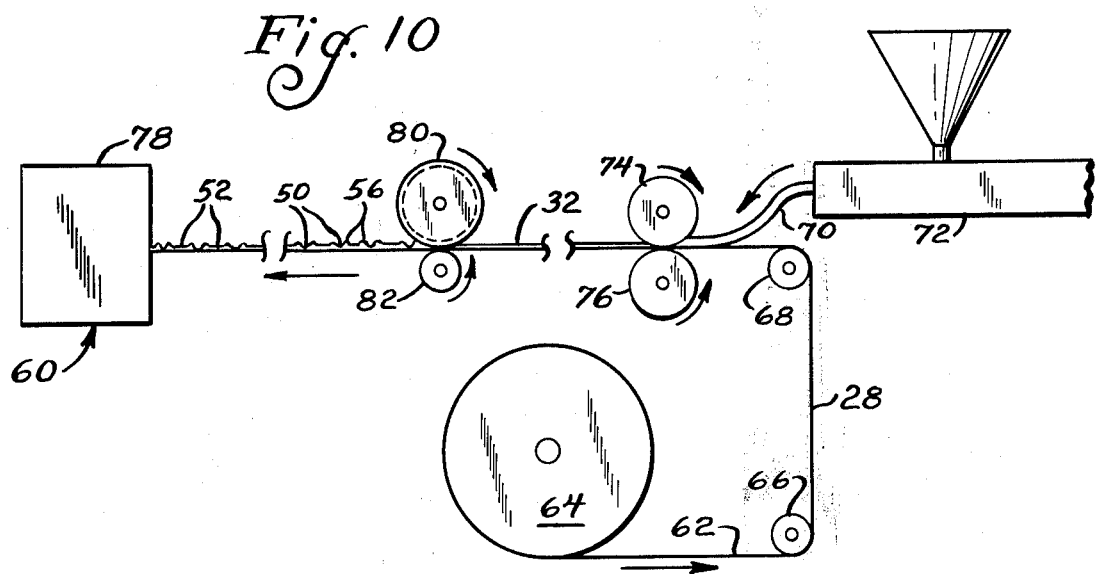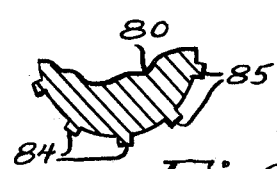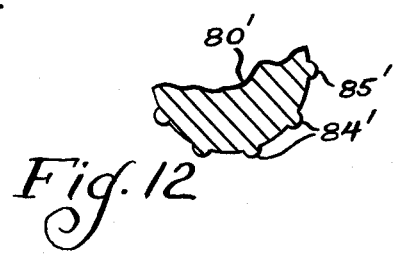

3,965,907

SURGICAL SPONGE

BACKGROUND OF THE INVENTION

The present invention relates to absorbent articles, and more particularly to surgical sponges.

Surgical sponges are commonly used during surgical procedures to absorb body fluids of the patient both inside the incision and around the site of surgery. Sponges of this nature are usually made of an open-meshed absorbent fabric, such as woven cotton, and become significantly reduced in size when they become wet during use.

It is important, of course, that all of such sponges be removed from the patient's body after surgery is complete and before the incision has been closed. Accordingly, it is a standard procedure for the surgical team to carefully count the sponges to reduce the possibility that a sponge may be left in the patient.

In spite of such safety measures, sponges have been occasionally lost, particularly when an unexpected emergency disrupted the normal operative routine such as counting, which is subject to human error, with the relatively small size of the sponges contributing to the possibility that they might be lost. It has become increasingly common, therefore, to provide the sponges with a flexible non-irritating insert which is opaque to X-rays. In case of a disputed or non-tallying sponge count in the operating room, or in case of unexpected or unexplainable post-operative discomfort on the part of the patient, a portable X-ray unit is brought to the patient and an X-ray exposure should reveal the presence or absence of a lost sponge. A negative plate should be reassurance to the surgeon that he and his operative team have not left a sponge in the patient.

In the past, such inserts have usually been placed loosely in the sponges by means of a superficial bond, such that they may inadvertently fall out of the sponges into the surgical cavity during the operation, or the inserts may break and a small portion may fall out of the sponges. Due to their relatively small size, such misplaced inserts, and particularly fragments of the inserts, in all likelihood will not be missed by the surgical team prior to closing the incision, and an X-ray of the patient will probably not be taken, since the count of all the reclaimed sponges indicates that nothing has been left in the patient. The lost insert may only be located at a later date when it produces a deleterious effect on the patient, and may only be removed at the cost of another operation.

Some difficulty has also been encountered in determining whether an X-ray photograph indicates the presence of such an insert in the patient, either attached or detached from the sponge. This follows since prior inserts have generally been provided in the form of a continuous long filament. The X-ray photograph may appear to show the presence of an insert, whereas a different object, such as a suture, has caused such appearance. Accordingly, the patient may be reopened to remove a sponge which is not present, or a sponge may be left in the patient if the person reading the plate erroneously concludes that the thread-like structure on the photograph is a suture.

SUMMARY OF THE INVENTION

A principal feature of the present invention is the provision of a surgical sponge of simplified construction which prevents mishaps in reclaiming sponges from a patient's body.

The sponge of the present invention comprises, an absorbent fabric, and an elongated X-ray detectable element located on the fabric.

A feature of the present invention is that the element forms an integral bond with the fibers in the fabric to prevent the element from becoming dislodged into the operative site during use of the sponge in an operation.

Another feature of the invention is that the element has a width of varying thickness through its length to provide a distinct pattern on an X-ray photograph.

Yet another feature of the invention is that the element has a varying thickness through its length to provide a distinct pattern on an X-ray photograph.

Thus, a feature of the present invention is that the distinctive pattern formed by the element on the X-ray photograph prevents mistake of the element for another object, such as a suture.

Still another feature of the invention is the provision of methods for making the surgical sponge of the present invention.

Further features will become more fully apparent in the following description of the embodiments of this invention and from the appended claims.

DESCRIPTION OF THE DRAWINGS

In the drawings:

FIG. 1 is a plan view of a surgical sponge of the present invention;

FIG. 2 is a fragmentary sectional view taken substantially as indicated along the line 2—2 of FIG. 1;

FIGS. 3–5 are perspective views illustrating steps in folding the sponge of FIG. 1 into a preferred configuration;

FIG. 6 is a fragmentary plan view of another embodiment of the sponge of the present invention;

FIG. 7 is a fragmentary plan view, on an enlarged scale, of the sponge of FIG. 6;

FIG. 8 is a fragmentary sectional view taken substantially as indicated along the line 8—8 of FIG. 7;

FIG. 9 is a fragmentary sectional view of another embodiment of the sponge of the present invention;

FIG. 10 is a diagrammatic view illustrating an apparatus for making sponges according to a method of the present invention;

FIG. 11 is a fragmentary sectional view of one embodiment of a patterning tool for the apparatus of FIG. 10;

FIG. 12 is a fragmentary sectional view of another embodiment of the patterning tool for the apparatus of FIG. 10;

DESCRIPTION OF THE PREFERRED EMBODIMENTS

Figure 13:
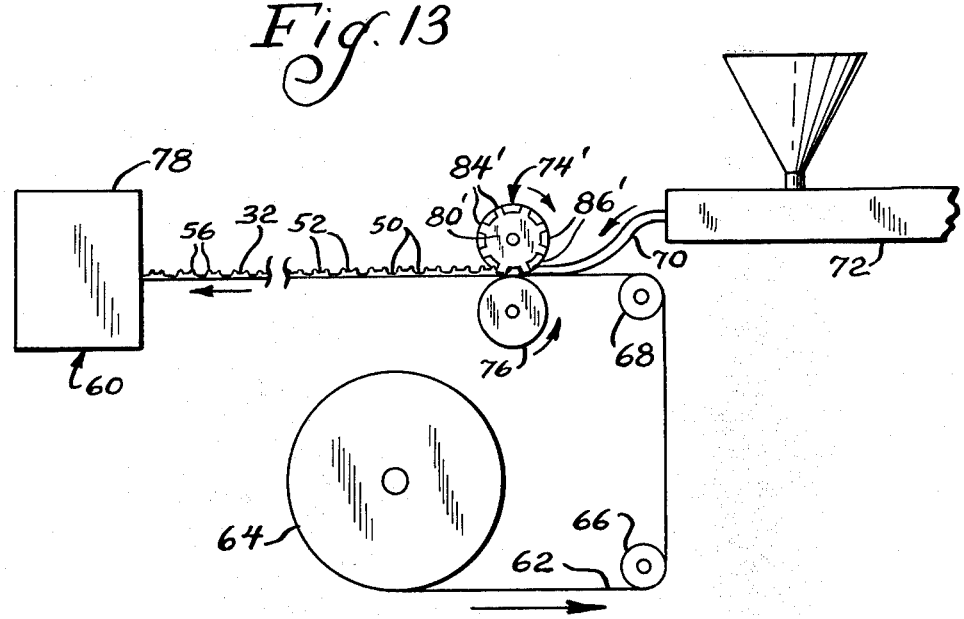
FIG. 13 is a diagrammatic view of another embodiment of apparatus for making sponges according to a method of the present invention.

Referring now to FIGS. 1 and 2, there is shown a surgical sponge generally designated 20 having a sheet 22 of a low-count gauze-like or open-mesh fabric, such as woven cotton. The sheet 22 has a pair of side edges 24a and 24b, a pair of end edges 26a and 26b connecting the side edges 24a and b, a front surface 28, and a back surface 30. The sponge 20 has an elongated flattened radiopaque element 32 extending laterally across the sheet 22 between the side edges 24a and b and spaced from the end edges 26a and b. The radiopaque element or filament 32 is integrally bonded to the fibers in the fabric of the sheet 22, as will be described below, to prevent dislodgment of the element 32 from the sponge 20 during use of the sponge in surgery. The element 32 may be made of a thermoplastic polymeric material containing a radiopaque material, such as barium sulfate, as known in the art. A suitable element 32 may have 4–5 parts of polymer to 6–5 parts of barium sulfate.

The sponge 20 may be folded into a preferred configuration as described below. As shown in FIGS. 1 and 3, an end section 33 of the sheet 22 is folded along a lateral fold line 35, with the front surface 28 of the end section 33 being positioned against an adjacent portion of the sheet, in order to place the edge 26a, which may be cut, remote the sides of the sponge. The front surfaces 28 of side sections 34a and 34b in the sheet 22 are then folded along longitudinally extending fold lines 38a and 38b against the front surfaces of intermediate sections 36a and 36b. Next, the back surfaces 30 of the inwardly folded side sections 34a and b are folded against each other along a longitudinally extending fold line 40. As shown in FIGS. 3 and 4, the longitudinally folded sheet 22 is then folded along a laterally extending central fold line 42 to position the back surfaces 30 of end sections 44a and 44b together. Finally, the end sections 44a and b of the laterally folded sponge 20 are laterally folded along a fold line 46 to reduce the length of the sponge, as illustrated in FIG. 5. In this configuration, the radiopaque element 32 is positioned inside the sponge, and the sheet 22 has been folded into a preferred shape for use in surgery.

Another embodiment of the sponge 20 of the present invention is illustrated in FIGS. 6–8, in which like reference numerals designate like parts. In this embodiment, the radiopaque element 32, which is preferably integrally bonded to fibers in the sheet 22, has a varying width and thickness throughout its length to provide a distinctive pattern of the element on an X-ray photograph. As shown in FIGS. 6 and 7, the element 32 has a plurality of zones 50 of increased width spaced along the length of the element. The element also has a plurality of regions 52 of reduced width intermediate the zones 52, with the regions 52 extending between the zones 50. The zones 50 may be spaced approximately an equal distance from each other along the length of the element 32. Accordingly, the alternating zones and regions of increased and reduced width will produce a recognizable pattern of varying width on an X-ray photograph to prevent mistake of the element 32 for a different object, such as a suture, which has a continuous width.

In addition, as illustrated in FIG. 6, longitudinally extending central portions 54 of the element zones 50 have a reduced thickness relative to the thickness of the regions 52. The element 32 may also have areas 56 of maximum thickness intermediate the zones 50 and regions 52, as shown. In the embodiment illustrated in FIG. 8, the central portions 54 of the zones 50 have an approximately uniform thickness. In another embodiment, as shown in FIG. 9, the central portions 54 of the zones 50 have a longitudinally extending arcuate configuration. In either event, the varying longitudinal thickness of the elongated element 32 will produce alternating areas or regions of lighter and darker contrast on an X-ray photograph to provide a recognizable pattern on the photograph. As is apparent, the central portions 54 of the zones 50 will appear the darkest on the X-ray photograph since there is less radiopaque material in the zones to prevent passage of X-rays through the element 32, thus permitting a relatively increased exposure to the X-ray plate in the zone portions 54. Similarly, the regions 52 will produce areas of intermediate contrast, while the areas 56 of the element 32 will appear the lightest on the photograph due to the increased amount of material in these areas. The sponges of FIGS. 6–9 may be folded as described in connection with the sponge of FIGS. 1–5.

An apparatus 60 for making the sponges 20 according to a method of the present invention is illustrated in FIG. 10. As shown, a web 62 of gauze-like or open-meshed absorbent material is unwound from a roll 64, and is passed over rollers 66 and 68, as indicated by the direction of the arrow in the drawing. A molten filament 70 of thermoplastic material containing a radiopaque material, such as barium sulfate, is formed by an apparatus 72, such as an extruder applicator, or similar piece of equipment, and is placed or dispensed by the apparatus 72 onto a surface 28 of the web 62. The web 62 and molten filament 70 are then passed between the nip of two rolls 74 and 76 to compress the molten filament 70 against the web 62, thus flattening the filament into the radiopaque element 32 and bonding the flattened element 32 to fibers of the web 62 when the element cools, such that an integral bond is thereby formed. The roll 76 may be made of a metal, and may be heated to further maintain the molten condition of the filament 70 and facilitate compression of the filament 70 in the nip between the rolls 74 and 76. The roll 74 may be made of a relatively soft material, such as rubber, which may have its outer surface coated with silicon to prevent sticking of the molten filament 70 to the outer surface of the roll 74. Alternatively, the roll 74 may be made of a metal, such as steel, and may have its outer surface coated with silicon to prevent sticking of the filament 70 to the roll. If desired, the web 62 and compressed element 32 may be passed directly into a section 78 of the apparatus 60, where the element 32 is cooled and the web 62 is slitted and folded into the sponges described in connection with FIGS. 1–5.

Alternatively, the web 62 and compressed element 32, which is still in a molten state, may be passed between a patterning tool 80 and a roll 82. As shown in FIG. 11, the patterning tool 80 has a plurality of laterally and outwardly extending elements 84 spaced peripherally around the outer surface of the tool 80. In this embodiment, the elements 84 have flattened ends 85 which further compress the molten element 32. The lower roll 82 may be made of a soft or rigid material, such as steel, which may or may not be heated, as desired. Thus, tool 80 and roll 82 form the zones 50 of increased width and zone central portions 54 of decreased and relatively uniform thickness in the element 32 described in connection with the sponge of FIGS. 6–8. Alternatively, the ends 85 of the extending elements 84 may be rounded, as shown in FIG. 12, to produce the zone central portions 54 of arcuate shape in the element 32, described in connection with the sponge of FIG. 9. Of course, the ends of the elements 84 may have any other suitable configuration, and in one embodiment the elements 84 may be spaced approximately an equal distance from each other to produce zones 50 in the element 32 which are spaced apart approximately an equal distance. The areas 56 of maximum thickness in the element 32, described in connection with FIGS. 6–9, are produced by longitudinal displacement of molten material from the central zone portions 54 as the molten element is compressed by the tool 80 and roll 82. Similarly, the zones 50 of increased width are produced by lateral displacement of molten material in the zones during compression by the tool 80 and roll 82. The web 62 and element 32 may then be passed into the section 78 where the element 32 is cooled, and the web 62 is slitted and folded, as previously described.

Figure 14:
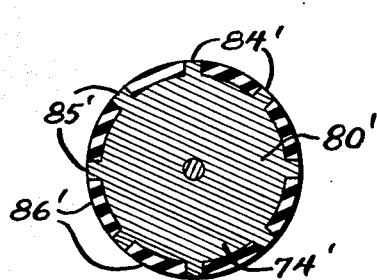
FIG. 14 is a sectional view of a roller, on an enlarged scale, for the apparatus of FIG. 13.

Another apparatus for making sponges according to a method of the present invention is illustrated in FIG. 13, in which like reference numerals designate like parts. In this embodiment, the web 62 and placed molten filament 70 are passed between rolls 74' and 76. The roll 76 is similar to the roll 76 described in connection with FIG. 10, and may be heated, if desired. However, the roll 74' has an inner patterning tool 80' of a rigid material, such as metal, having a plurality of laterally and outwardly extending elements 84' spaced peripherally around the tool 80', as shown in FIGS. 13 and 14. The roll 74' also has a plurality of laterally extending spacers 86' of a soft material, such as rubber, extending between the rigid elements 84'. The elements 84' may have flattened ends 85', as shown, or any other suitable configuration, as desired. Thus, as the molten filament 70 passes between the nip of the rolls 74' and 76, the rigid elements 84' compress the filament 70 to a greater extent than the soft spacers 86', and in this particular embodiment produce an element 32 of varying width and thickness as described in connection with FIGS. 6–9, with compression of the filament being accomplished with a single set of rolls. The element 32 and web 62 may be passed into the section 78 for cooling, slitting, and folding, as previously described.

Thus, according to methods of the present invention a molten filament of X-ray detectable material is placed on an absorbent fabric, and the molten filament is compressed into the fabric, after which the compressed filament in cooled to integrally bond the element to fibers in the fabric. According to another method of the invention, spaced zones of the molten filament are further compressed to provide a distinctive pattern of the filament for an X-ray photograph.

The foregoing detailed description is given for clearness of understanding only, and no unnecessary limitations should be understood therefrom, as modifications will be obvious to those skilled in the art.

We claim:

1. A surgical sponge, comprising an absorbent fabric; and
an elongated radiopaque filament integrally bonded to fibers in said fabric to prevent dislodgment of said filament during use of said sponge, said filament having a varying dimensional configuration along the length of filament to provide a distinctive pattern of the filament on an X-ray.

2. The sponge of claim 1 wherein said filament is elongated and extends substantially between opposed marginal edges of said fabric.

3. The sponge of claim 2 wherein said fabric includes a pair of edges connecting said opposed edges, and the elongated filament is spaced from said pair of edges.

4. The sponge of claim 1 wherein said filament comprises a thermoplastic material compressed in a molten condition into said fabric.

5. A surgical sponge, comprising:
an absorbent fabric; and
an elongated radiopaque filament positioned on said fabric and having a varying width along the length of filament to provide a distinctive pattern of the filament on an X-ray.

6. The sponge of claim 5 wherein said filament has a plurality of zones of increased width spaced along the length of the filament and a plurality of regions of reduced width intermediate said zones.

7. The sponge of claim 6 wherein said zones are spaced from each other approximately an equal distance along the length of said filament.

8. The sponge of claim 5 wherein said filament is integrally bonded to fibers in said fabric.

9. A surgical sponge, comprising:
an absorbent fabric; and
an elongated radiopaque element positioned on said fabric and having a varying thickness along the length of element to provide a distinctive pattern of the element on an X-ray.

10. The sponge of claim 9 wherein said element has a plurality of zones of reduced thickness spaced along the length of said element, and a plurality of regions of increased thickness intermediate said zones.

11. The sponge of claim 10 wherein said element includes a plurality of areas of maximum thickness intermediate said regions and zones.

12. The sponge of claim 10 wherein said zones include longitudinally extending portions having an arcuate configuration.

13. The sponge of claim 10 wherein said zones include longitudinally extending portions having approximately uniform thickness.

14. The sponge of claim 9 wherein said element is integrally bonded to fibers in said fabric.

* * * * *